(12) United States Patent
Cunningham

(10) Patent No.: US 9,061,626 B2
(45) Date of Patent: Jun. 23, 2015

(54) LIFTING SYSTEM FOR LIFTING A PERSON INTO A VEHICLE

(71) Applicant: John Cunningham, Hurricane, WV (US)

(72) Inventor: John Cunningham, Hurricane, WV (US)

( * ) Notice: Subject to any disclaimer, the term of this patent is extended or adjusted under 35 U.S.C. 154(b) by 0 days.

(21) Appl. No.: 14/167,522

(22) Filed: Jan. 29, 2014

(65) Prior Publication Data

US 2014/0140796 A1    May 22, 2014

Related U.S. Application Data

(60) Division of application No. 13/905,743, filed on May 30, 2013, which is a division of application No. 12/662,249, filed on Apr. 7, 2010, now Pat. No. 8,474,161, which is a continuation of application No. 29/347,301, filed on Nov. 25, 2009, now Pat. No. Des. 630,268.

(60) Provisional application No. 61/202,801, filed on Apr. 7, 2009.

(51) Int. Cl.

| *B60P 1/54* | (2006.01) |
| *B60L 11/18* | (2006.01) |
| *B66C 23/18* | (2006.01) |
| *B66C 23/28* | (2006.01) |
| *B66C 23/36* | (2006.01) |
| *E02F 3/96* | (2006.01) |
| *E02F 9/16* | (2006.01) |

(Continued)

(52) U.S. Cl.
CPC ............... *B60P 1/5438* (2013.01); *B60L 11/18* (2013.01); *B60L 2200/40* (2013.01); *B66C 23/18* (2013.01); *B66C 23/28* (2013.01); *B66C 23/36* (2013.01); *E02F 3/964* (2013.01); *E02F 9/166* (2013.01); *E02F 9/2025* (2013.01); *F41H 7/005* (2013.01); *F41H 7/02* (2013.01); *F41H 7/04* (2013.01); *F41H 11/20* (2013.01); *F41H 11/22* (2013.01); *F41H 11/28* (2013.01); *Y02T 10/7005* (2013.01); *B05B 15/00* (2013.01); *G01N 33/227* (2013.01)

(58) Field of Classification Search
CPC .............................. B60P 1/5409; B60P 1/5442
USPC .......................................................... 414/542
See application file for complete search history.

(56) References Cited

U.S. PATENT DOCUMENTS

| 1,614,769 | A | * | 1/1927 | Amsler | .......................... | 414/542 |
| 2,504,232 | A | * | 4/1950 | Smith | ........................... | 414/542 |

(Continued)

*Primary Examiner* — Jonathan Snelting
(74) *Attorney, Agent, or Firm* — Jean C. Edwards, Esq.; Edwards Neils PLLC

(57) ABSTRACT

A lifting system for lifting a person into a construction vehicle for operation thereof, including a wheelchair compatible seat which detaches from a wheelchair; and a lifting mechanism including a rack and pinion mechanism, mounted to a top portion of the construction vehicle, a rack portion of the rack and pinion mechanism being movable outwardly and inwardly with respect to a side of the construction vehicle, a crane assembly disposed on the rack portion and having a lifting cable with a clip mounted on the end, and a lifting harness connected to the wheelchair compatible seat and connected to the clip, wherein when the clip is connected to the harness, the crane assembly of the lifting mechanism is activated and the wheelchair compatible seat is lifted up from the wheelchair, moved inwardly by the rack portion to a seat position of the construction vehicle, and lowered into the seat position.

3 Claims, 18 Drawing Sheets

(51) Int. Cl.

| | | |
|---|---|---|
| *E02F 9/20* | (2006.01) | |
| *F41H 7/00* | (2006.01) | |
| *F41H 7/02* | (2006.01) | |
| *F41H 7/04* | (2006.01) | |
| *F41H 11/20* | (2011.01) | |
| *F41H 11/22* | (2011.01) | |
| *F41H 11/28* | (2011.01) | |
| *B05B 15/00* | (2006.01) | |
| *G01N 33/22* | (2006.01) | |

(56) References Cited

U.S. PATENT DOCUMENTS

| | | | |
|---|---|---|---|
| 2,918,738 A | 12/1959 | Barr | |
| 4,222,186 A | 9/1980 | Molby | |
| 4,242,030 A * | 12/1980 | Clement | 414/462 |
| 4,245,947 A * | 1/1981 | Clement | 414/462 |
| 4,524,674 A | 6/1985 | Gilvydis | |
| 4,574,685 A | 3/1986 | Sanborn et al. | |
| 4,600,069 A | 7/1986 | Oswald et al. | |
| 4,648,305 A | 3/1987 | Elspass | |
| 4,714,140 A | 12/1987 | Hatton et al. | |
| 4,769,700 A | 9/1988 | Pryor | |
| 4,806,060 A * | 2/1989 | Molski | 414/462 |
| 4,810,160 A * | 3/1989 | Emiliani et al. | 414/543 |
| 5,158,146 A | 10/1992 | Fuller | |
| 5,338,147 A * | 8/1994 | Kucharczyk et al. | 414/542 |
| 5,452,640 A | 9/1995 | Bovee et al. | |
| 5,622,235 A | 4/1997 | Merritt | |
| 5,727,481 A | 3/1998 | Voorhees et al. | |
| 5,830,752 A | 11/1998 | Bruso | |
| 5,836,398 A | 11/1998 | White | |
| 5,936,185 A | 8/1999 | Tokuni | |
| 5,974,348 A | 10/1999 | Rocks | |
| 6,029,750 A | 2/2000 | Carrier | |
| 6,102,469 A | 8/2000 | Shambeau et al. | |
| 6,273,668 B1 * | 8/2001 | Kameda | 414/462 |
| 6,282,477 B1 | 8/2001 | Gudat et al. | |
| 6,435,071 B1 | 8/2002 | Campbell | |
| 6,443,490 B2 | 9/2002 | Webb | |
| 6,584,881 B1 | 7/2003 | Boudreau et al. | |
| 6,619,177 B1 | 9/2003 | Hansen et al. | |
| 6,621,764 B1 | 9/2003 | Smith | |
| 6,798,343 B2 | 9/2004 | Carrier et al. | |
| 6,862,509 B2 | 3/2005 | Rau et al. | |
| 7,086,318 B1 | 8/2006 | Darnall | |
| 7,565,941 B2 | 7/2009 | Cunningham | |
| 2007/0154295 A1 * | 7/2007 | Kuriakose | 414/546 |
| 2007/0189886 A1 * | 8/2007 | Chaddock | 414/498 |

* cited by examiner

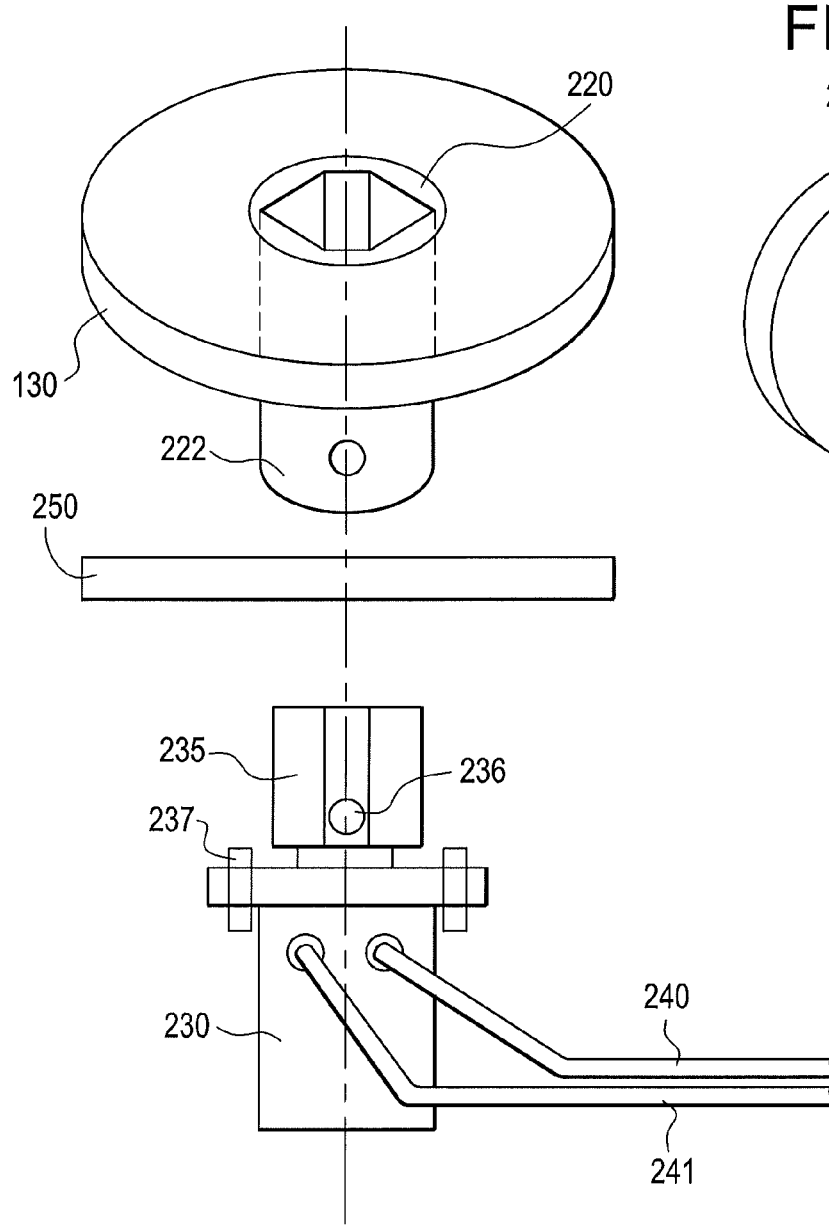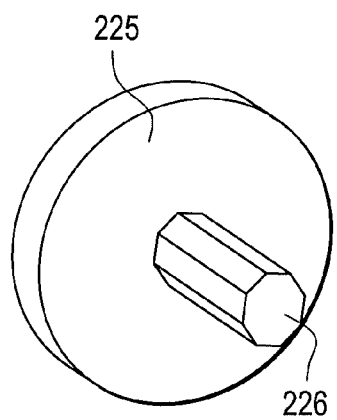

LIFTING SYSTEM FOR LIFTING A PERSON INTO A VEHICLE

CROSS REFERENCE TO RELATED APPLICATIONS

The present application is a Divisional Application of U.S. patent application Ser. No. 13/905,743, filed May 30, 2013, which is a Divisional Application of U.S. patent application Ser. No. 12/662,249, filed Apr. 7, 2010, now U.S. Pat. No. 8,474,161, which issued Jul. 2, 2013, which is a continuation of U.S. Design patent application Ser. No. 29/347,301, filed Nov. 25, 2009, now U.S. Design Pat. No. D630,268, which issued Jan. 4, 2011, and claims priority from U.S. Provisional Patent Application No. 61/202,801, filed Apr. 7, 2009, the contents of all of which are herein incorporated by reference in their entirety.

FIELD OF THE INVENTION

The present disclosure relates generally to multitask vehicles and, more particularly, to multitask vehicles for military use, rescue, transport, and explosive detection and removal.

BACKGROUND OF THE INVENTION

There is an ever-increasing threat of Improvised Explosive Devices (IEDs), suicide bombers, car bombs, and nuclear/biological/chemical devices being used against both military personnel and civilian targets alike. Notwithstanding this ongoing threat, there is no vehicular design that can quickly be adapted to support such a wide range of threats. Moreover, when severe natural disasters such as earthquakes, hurricanes, tsunamis, etc., occur at diverse places around the world, U.S. Soldiers are often called upon to provide humanitarian assistance. Thus, the soldiers need an adaptable mobile platform that is simple but versatile. Other disasters, such as a mine collapse, could also benefit from a versatile, multitask vehicle.

With wounded veterans returning from various conflicts around the world, as well as injured civilians, mobile platforms that are easily accessible would also be beneficial.

Still further, explosive/landmine detection devices that can be easily integrated with such a mobile platform would result in saved lives and cost savings, especially in regions of indigenous populations throughout the world.

SUMMARY OF THE INVENTION

Apparatuses consistent with the present disclosure relate to a multitask vehicle having a modified frame assembly in order to permit secondary systems or assemblies to be quickly added and removed with respect to a common vehicle platform. Thus, the multitask vehicle can change its function to meet an immediate need or threat.

Moreover, apparatuses consistent with the present disclosure provide for a multitask vehicle that has both robotic and manual controls.

Moreover, apparatuses consistent with the present disclosure allow for a multitask vehicle that can be used for mine rescue, and includes a series of indicator lights that are set to warn of dangerous gas levels of gases such as oxygen, methane, carbon-dioxide, carbon-monoxide, or the like.

Moreover, apparatuses consistent with the present disclosure provide for a multitask vehicle having an integrated design that permits the vehicle to be righted if it has flipped over, and a series of modular internal compartments that can be joined together, and also added or removed to modify the vehicle body.

Moreover, apparatuses consistent with the present disclosure provide for a system to assist a wounded soldier or injured/paralyzed civilian that can be added to a standard commercial vehicle or to the multitask vehicle according to the present invention.

Still further, apparatuses consistent with the present disclosure provide for a sensor system for detecting, for example, IEDs or landmines, that can be added to a standard commercial vehicle or to the multitask vehicle according to the present invention.

According to one aspect, the present disclosure provides a multitask, motorized vehicle, including: a vehicle body having a rigid frame with a pair of front wheels and a pair of rear wheels mounted thereon; and a rotary mounting platform disposed on top of the vehicle body and which has a mounting portion being configured to interchangeably mount and remove various secondary systems or components, thereby permitting the multitask, motorized vehicle to change functions.

According to another aspect of the present disclosure, the secondary systems or components include at least one of a high performance gun platform, a missile platform, a speaker platform, a multi-light platform, an unmanned aerial vehicle (UAV) launch platform, a robot arm, a multiple imaging platform, or a multiple gun platform.

According to another aspect of the present disclosure, a lifting system is provided in combination with a construction vehicle, for lifting a person into the construction vehicle for operation thereof, including: a wheelchair compatible seat which is operative to detach from a wheelchair; and a lifting mechanism comprising a rack and pinion mechanism that is mounted to a top portion of the construction vehicle, a rack portion of the rack and pinion mechanism being movable outwardly and inwardly with respect to a side of the construction vehicle, a crane assembly disposed on the rack portion of the rack and pinion mechanism and having a lifting cable with a clip mounted on the end, and a lifting harness connected to the wheelchair compatible seat and operative to be connected to the clip, wherein when the clip is connected to the harness of the wheelchair compatible seat, the crane assembly of the lifting mechanism is activated and the wheelchair compatible seat is lifted up from the wheelchair, moved inwardly by the rack portion to a seat position of the construction vehicle, and then lowered into the seat position.

The present disclosure also contemplates a sensor system for detecting one of Improvised Explosive Devices (IEDs), landmines or other buried explosives, the sensor system being mounted in place of a standard backhoe digging bucket, the sensor system including: a mounting portion having arc swing points for hanging the sensor system on a backhoe arm, and a holding pin opening for receiving a holding pin when positioned in a mounting position on the backhoe arm; and an electronic sensor wand arm assembly mounted to the mounting portion.

According to another aspect of the present disclosure, the sensor system includes a spring assembly including a spring mounted at one end to an outer plate adjustably disposed at a rear of the mounting portion, and an adaptor movably engaged at a front of the mounting portion and having a rod extending from an inner side thereof, the adaptor having an outer side which is connected to the electronic sensor wand arm assembly, wherein the other end of the spring is attached to the rod, such that adjustment of a tension of the spring allows for lateral movement of the electronic sensor wand arm assembly, thereby to protect the electronic sensor wand arm assembly as the backhoe arm swings from side to side.

Those skilled in the art will appreciate the scope of the present invention and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the invention, and together with the description serve to explain the principles of the invention.

FIGS. 2B and 2C illustrate an exemplary connection for the secondary components to the multitask vehicle;

DETAILED DESCRIPTION OF THE PREFERRED EMBODIMENTS

The embodiments set forth below represent the necessary information to enable those skilled in the art to practice the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

As indicated above, apparatuses and systems consistent with the present invention provide for multitask vehicles for military use, rescue, transport, and explosive detection and removal. While exemplary embodiments are often discussed below in the context of a military application, one skilled in the art will appreciate that apparatuses and systems suitable for civilian use such as, but not limited to, humanitarian, mining and mine rescue, rescue in general, construction, etc., are also contemplated.

A more detailed description of the apparatuses and systems consistent with the present disclosure will now follow with reference to the accompanying drawings.

Figure 1:
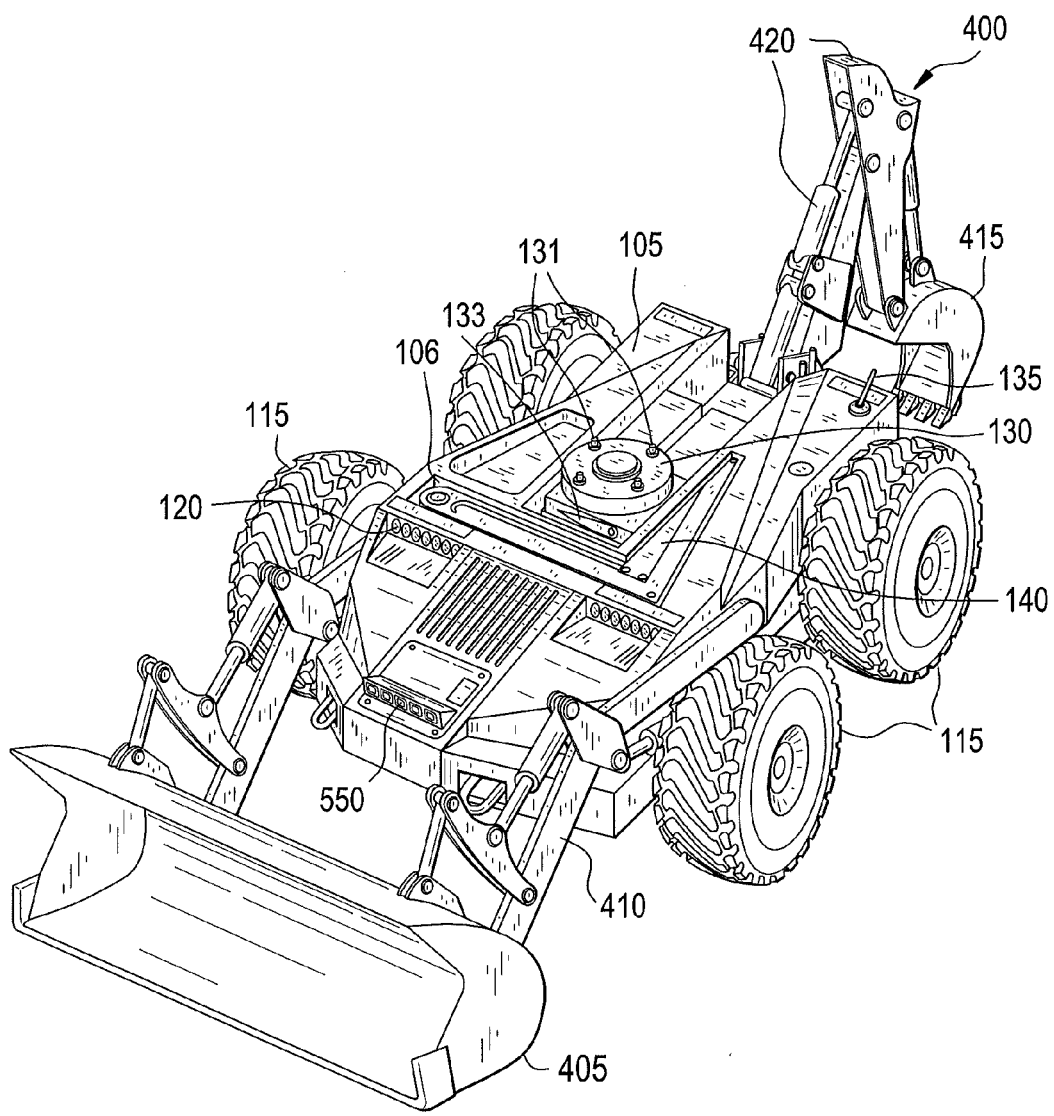
FIG. 1 illustrates a multitask vehicle having a modified frame assembly in order to permit secondary systems or assemblies to be quickly added and removed with respect to a common vehicle platform, according to an exemplary embodiment of the present disclosure.

FIG. 1 illustrates an exemplary embodiment of a multitask vehicle 100 having a modified frame assembly in order to permit secondary systems or assemblies to be quickly added and removed with respect to a common vehicle platform. This, in turn, permits the multitask vehicle to change its function to meet an immediate need or threat. More specifically, the multitask vehicle is an inexpensive, lightweight, easily transportable vehicle that is designed for a wide range of temperature environments, is able to carry its own service parts, and has extremely low maintenance and service needs. As will be described in more detail below, the secondary systems or components include task-specific tools, sensors, and weapons that can quickly be removed and replaced by a user, such as a soldier in a hostile environment (for example, in less than five minutes).

In FIG. 1, the multitask vehicle 100 includes a vehicle body 105 that includes a rigid, for example, steel frame and body panels. The steel frame and body panels provide strength and protection for the internal components and allow the secondary or auxiliary systems or components, which will be described in more detail below, to be easily added or removed from the vehicle body 100.

The multitask vehicle 100 is self-propelled by an engine or motor 110 powered by, such as, but not limited to: diesel, gasoline, electric, battery, or pneumatic, with horse power (HP) ranging from 20 to 55. The diesel capacity typically will exceed 8 hours of operation, but may optionally exceed 30 hours of operation if desired. The cooling system may be air, water, or oil for the engine and hydraulic system. The air filter is designed for dusty environments and long operational use.

The transmission system may be 100% hydraulic, and the driveline power may be 2WD or 4WD. The drive axles may be: front-hydraulic, and the rear-limited slip, disconnect type, or hydraulic. The steering system may be a standard-automotive, or optionally a crab and zero turn radius. The multitask vehicle 100 can be towed without a trailer, or can conveniently fit in the bed of an 8' pickup truck, or on a trailer. The tires 115 may be full size construction tires, automotive tires, or industrial tires, and further may be solid or cushion to help with landmines.

The multitask vehicle 100 has both robotic or manual controls. More specifically, the vehicle control system may be manual, wireless, or cable control. FIG. 1 shows an antenna 135 for wireless control of the vehicle 100. The remote control receiver may be located at any convenient location and preferably inside the vehicle 100 and then simply connected to the antenna 135 by a suitable electrical wire or cable. The robotic or remote control system typically exceeds 1500 feet, but the range, as well as the remote control frequency, may be options that can be varied, as needed. A suitable remote control/manual control is described in my U.S. Pat. No. 7,565,941, issued on Jul. 28, 2009, the contents of which are incorporated herein by reference in their entirety.

Other optional features include: vehicle operational lights 120 in the front and rear; an armament system, with the vehicle able to carry over 1000 pounds of ammunition; a camera system quickly adapted to the steel frame and which includes at least one of a thermal camera, a motion camera, a digital camera, a near infrared camera; an audio system, with the capability of producing other vehicle sounds and communication such as, for example, the sound of a tank, or of marching troops, or verbal announcements or instructions, within a predetermined range of the multitask vehicle 100; an auxiliary hydraulic system, with the capability of allowing secondary tools; and customized vehicle color for particular environment.

Moreover, the maintenance and service of the multitask vehicle is minimal and is based on automotive design, with support and repair components preferably being carried within the vehicle itself.

Figure 2A:
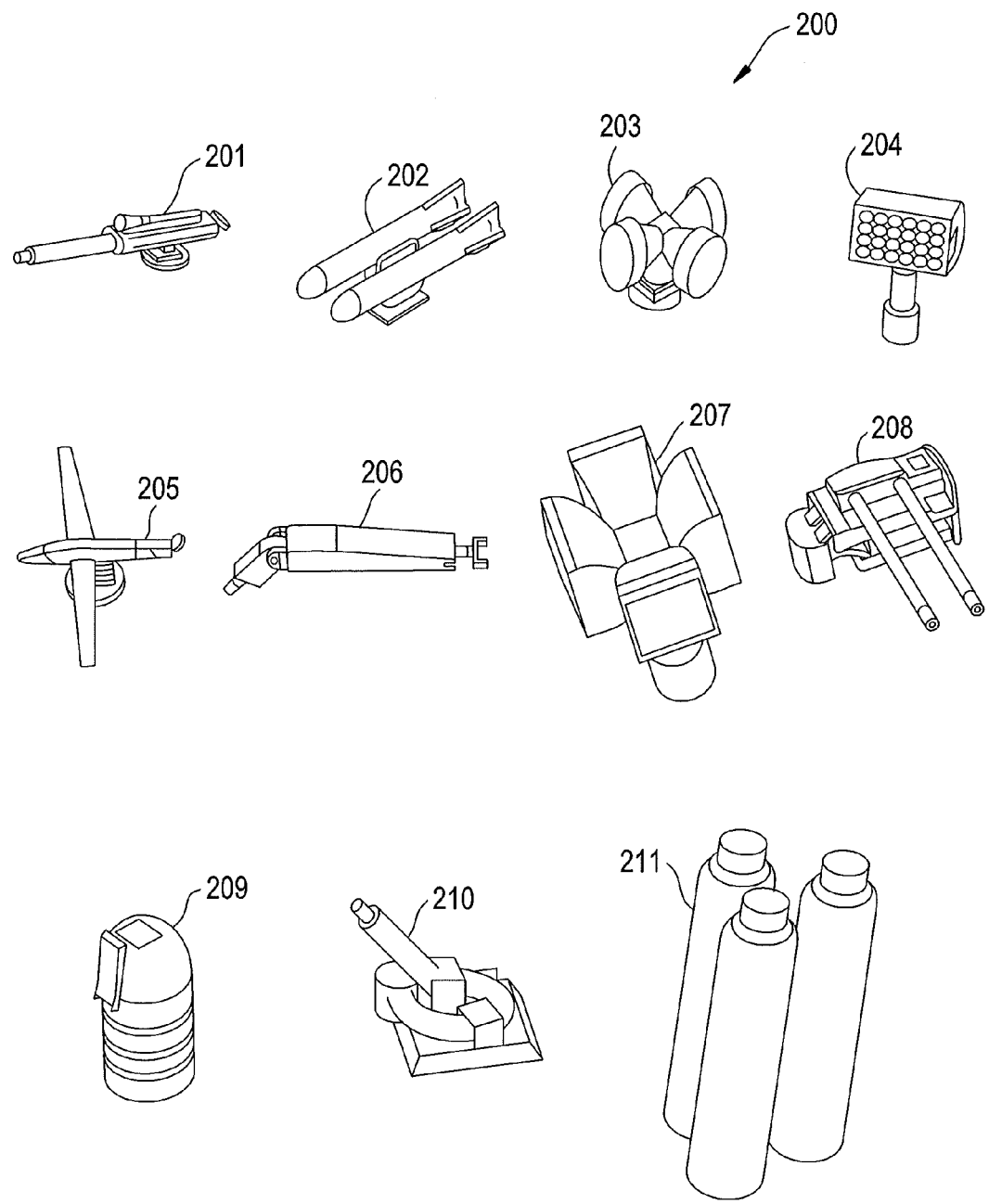
FIG. 2A illustrates various exemplary secondary components for the multitask vehicle.

The multitask vehicle 100 includes a rotary mounting platform 130 which has a mounting portion, for example, upstanding threaded mounting studs 131 for quickly and interchangeably mounting and removing the various secondary systems or components 200 as shown in FIG. 2A. The secondary components 200 have mounting bases or base plates with corresponding openings for receiving the mounting studs 131, as discussed in more detail below. While FIG. 1 shows the mounting portion using upstanding studs 131, other mounting configurations could be used. For example, as shown in FIGS. 2B and 2C, the rotary mounting platform 130 can have a centrally located, six sided hex tubing 220 serving as the female connection, whereas each of the secondary components 200 have a mounting base plate or base 225 with a corresponding hex male shaft 226 extending from the bottom thereof for insertion into the hollow female hex tubing 220 of the mounting platform 130 for quick connection and removal. The connection can rely solely on the interference fit between the female hex tubing 220 and the male hex shaft 226, or can also use the studs and bolts to further fasten the secondary systems 200 to the mounting platform 130. A hydraulic rotational drive motor 230 may be used to rotate the rotary mounting platform 130 and includes a hex drive or output shaft portion 235 which is inserted into a lower part 222 of the female hex tubing which is then locked to the drive shaft portion 235 by a locking pin 236. The hydraulic rotational drive motor 230 is positioned within the multitask vehicle 100 such as by bolts 237 and includes hydraulic fluid drive lines 240 and 241 for input and output of the hydraulic fluid. A rotary encoder 250 can be used to provide position feedback for true position information. The rotary encoder 250 is positioned between the mounting platform 130 and the drive shaft 235.

In a military setting, the secondary systems or components 200 may include, for example, a high performance gun platform 201, a missile platform 202, a speaker platform 203, a multi-light platform 204, an unmanned aerial vehicle (UAV) launch platform 205, a robot arm 206, a multiple imaging platform 207, and a multiple gun platform 208. Clearly, the secondary systems or components 200 are not limited to those mentioned above, and other secondary systems useful in a military context are contemplated by the present invention. Moreover, as will be discussed in more detail below in the context of the mine rescue multitask vehicle, other secondary components in addition to the robot arm 206 and the imaging platform 207, such as a camera 209, a water spout 210, and an oxygen tank or tanks 211, that would be useful in a mine rescue situation are also contemplated by the present invention. Each of the platforms has a mounting base plate or base that either has the hex tube 220 and hex shaft 226 connection described above, or has through-holes which are aligned with the threaded mounting studs 131 such that the studs extend through to permit bolts to be quickly threaded on the studs, or a combination of both type of connections to securely mount the particular secondary system 200. An indicating arrow 133 can be disposed on the multitask vehicle 100 near the mounting platform 130 to ensure proper alignment of the secondary systems 200 when being mounted to the multitask vehicle 100.

Figure 5:
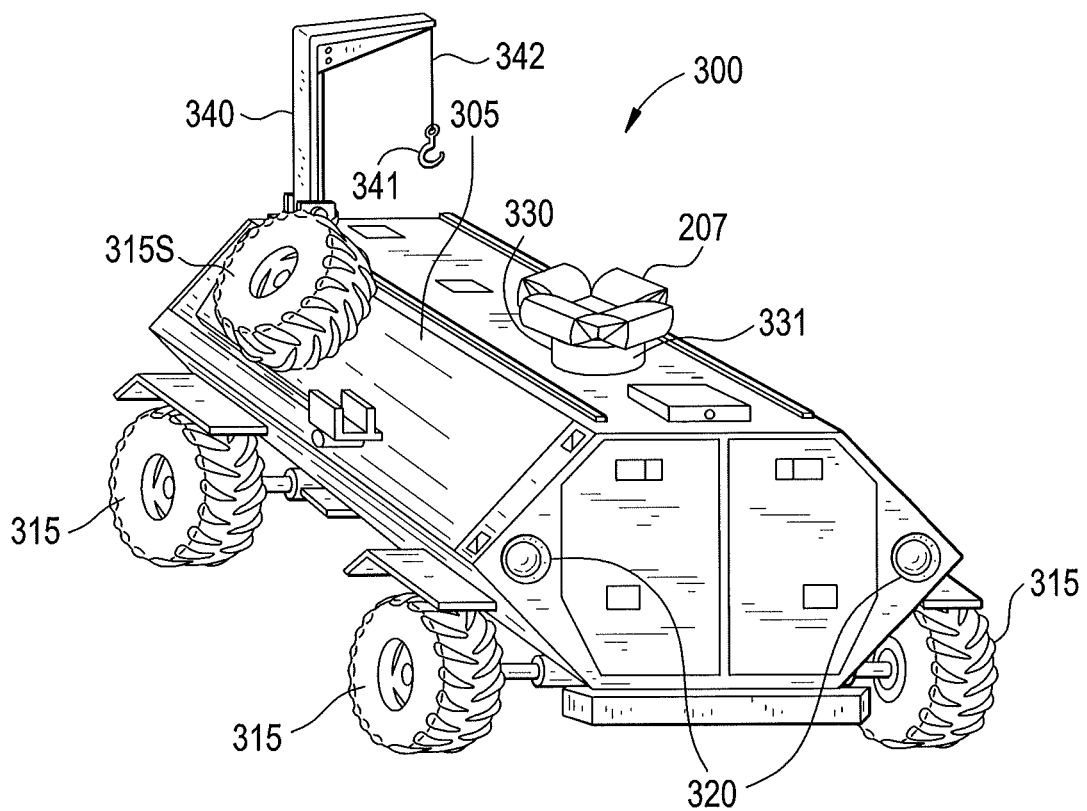
FIG. 5 shows a further embodiment of the multitask vehicle having a sloped wall body design according to an illustrative embodiment.

As shown in FIG. 1, the multitask vehicle 100 may also include a jib crane 140. FIG. 1 shows the jib crane 140 in a stowed position within a cut-out portion 106 of similar shape on top of the multitask vehicle 100 so as to be flush with the vehicle's top. Although not shown in FIG. 1, the embodiment of FIG. 5 shows a similar jib crane 340 raised in an upright operational position, with a lifting hook 341 being tethered at the end of a cable 342. The cable 342 may be fed out or reeled-in in a standard fashion by a motor and reel hub (not shown) disposed within the multitask vehicle 100. Accordingly, the jib crane 140 can be used to mount/demount needed accessories to and from the multitask vehicle 100 without the need for a separate secondary vehicle for loading and unloading.

As best shown in FIG. 1, the multitask vehicle 100 may also include a front end loading bucket 405 controlled with a standard hydraulic lifting mechanism 410. While the front end loading bucket 405 is shown in FIG. 1, other earthmoving attachments such as a dozer blade (not shown) may instead be mounted on the front end of the multitask vehicle 100. Moreover, a backhoe attachment 400 with a backhoe bucket 415 and standard backhoe hydraulic control arms 420 may be included at the rear of the multitask vehicle 100.

Figure 3:
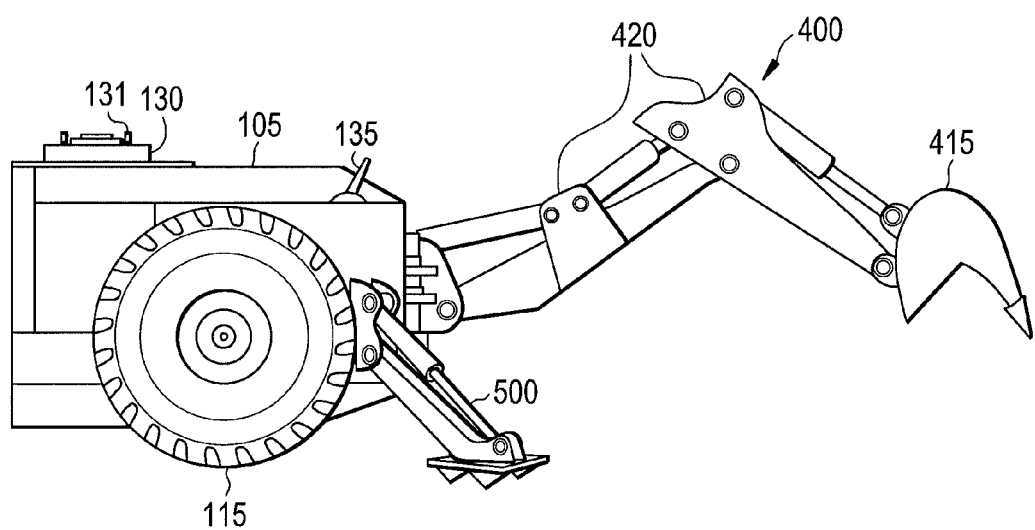
FIG. 3 illustrates the backhoe attachment for the multitask vehicle of FIG. 1 in an extended position.

FIG. 3 shows the backhoe attachment 400 in an extended position, with a pair of hydraulically operated stabilizer feet 500 (only one of which is visible in FIG. 3) shown in an operational position suitable for stabilizing the multitask vehicle 100 while it is digging.

Figure 4:
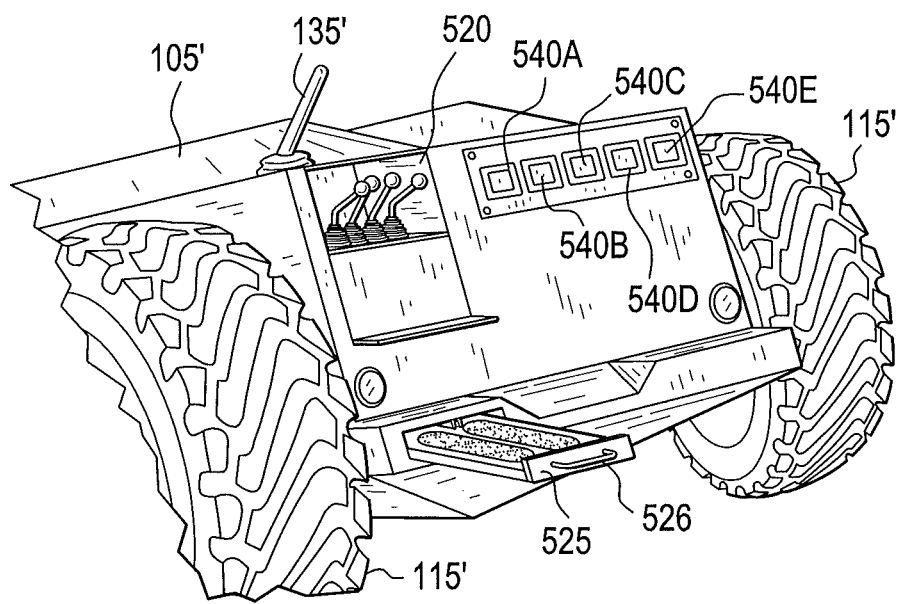
FIG. 4 shows a rear portion of an alternative embodiment of the multitask vehicle which may be used in environments such as for mine rescue according to an illustrative embodiment.

FIG. 4 shows a rear portion of an alternative embodiment of the multitask vehicle 100' which, as mentioned above, may be used in environments such as for mine rescue, such as in a coal mine rescue situation, and for rescue in general such as after an earthquake. Like elements are designated with like reference numerals except that a prime sign is included. As noted above, the multitask vehicle 100' includes a rotary mounting platform similar to platform 130 which has, for example, upstanding threaded mounting studs for quickly mounting and removing the various secondary systems or components 200 as shown in FIG. 2A. In this case, the non-military secondary systems or components 200 such as a robot arm 206, a camera 209, a water spout 210, a multi-light platform 204, and the like can be interchangeably mounted to the rotary mounting platform by, for example, internally threaded bolts and/or the hex tubing 220 and hex shaft 226 connection. Also, oxygen 211 can be included in, for example, coal mine or earthquake rescue situations.

The multitask mine rescue vehicle 100' comprises an autonomous vehicle that can operate along a set path, and has both robotic and manual controls. More specifically, as shown in FIG. 4, at the rear of the vehicle 100', a set of manual controls 520, such as a plurality of control knobs, are provided along with a slide out step 525 with pull handle 526 for a rescue worker/miner to stand and manually operate the vehicle 100', for example, if the remote control system fails. An antenna 135' for wireless control of the remote control system is shown adjacent to the manual controls 520.

A series of colored indicator or warning lights 540A-540E are provided to indicate dangerous levels of specific gases such as, for example, oxygen, methane, carbon-dioxide, carbon-monoxide, or the like. The indicator lights can also be positioned at the front of the vehicle 100'. Other indicator lights such as for indicating battery strength may be included. As noted above, the vehicle 100' can carry a support oxygen system 211 to assist rescue crews. As shown in FIG. 1, the indicator lights 550 may be included in the military multitask vehicle 100, the indicator lights being shown at the front of the vehicle.

FIGS. 5-8 show a further embodiment of the multitask vehicle 300 having a sloped wall body design 305 for deflecting small arms fire as disclosed in FIG. 4 of my U.S. Pat. No. 7,565,941. The multitask vehicle 300 includes a rotary mounting platform 330 which has, for example, upstanding threaded mounting studs 331 and/or the hex tubing connection for quickly mounting and removing the various secondary systems or components 200 as shown and described above with respect to FIG. 2A. FIG. 5 shows the multiple imaging platform 207 as an example. Having the ability to quickly modify the vehicle 300 gives the vehicle a wider range of uses. With such modifications, the secondary systems 200 can be added and changed in minutes, thus the vehicle can change its function to meet an immediate need or threat. Such secondary systems 200 may include but are not limited to: weapons, speakers, cameras, work lights, sensors, etc. The vehicle 300 is also robotically and/or manually operated, thus freeing the operator from potential danger.

As shown in FIG. 5, the multitask vehicle 300 may also include a jib crane 340. As noted above, FIG. 5 also shows the jib crane 340 in a stowed position on the side of the multitask vehicle 300 below the spare tire 315S. As with the multitask vehicle 100 of FIG. 1, the tires 315 may be full size construction tires, automotive tires, or industrial tires, and further may be solid or cushion to help with landmines. Vehicle operational lights 320 may be positioned in the front and rear. To remove the jib crane 340, the assembly is unhooked from the vehicle 300, turned 90 degrees and slid out the rear of the vehicle. Note that this allows the spare tire 315S to remain in position. To reinstall the jib crane 340 assembly, the steps are done in reverse. Having the jib crane 340 negates the need for a support vehicle. The jib crane 340 assembly can also be mounted in each of the four corners of the upper platform. This allows for ease of adding/removing functions.

The integration of secondary devices gives a wide range of options and use to the vehicle. Other secondary devices such as a backhoe digger, front loader, (as shown in FIG. 1), etc., can be added to the primary vehicle 300.

Figure 6:
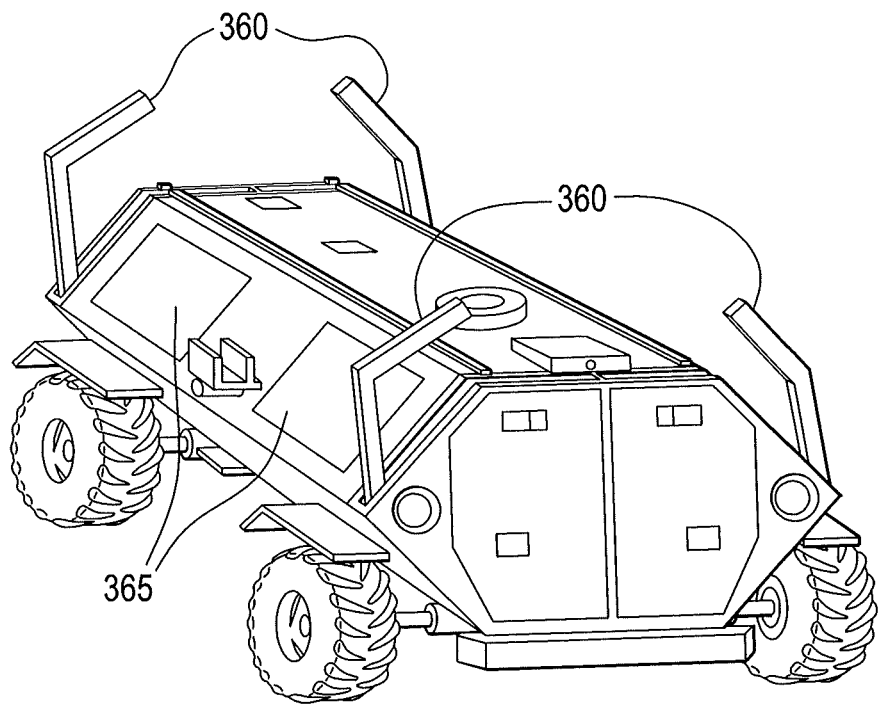
FIGS. 6 and 7 show a tandem set of levers that can be incorporated into the front and rear upper platform of the vehicle of FIG. 5.
Figure 7:
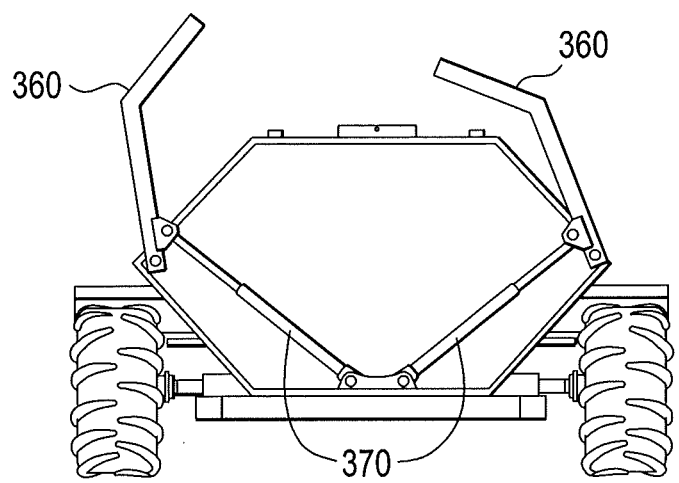

Since the vehicle 300 will normally be subjected to terrain that may cause it to flip over, or be flipped over by explosions, as shown in FIGS. 6 and 7, a tandem set of levers 360 can be incorporated into the front and rear upper platform in order to add to the performance of the vehicle 300. The levers 360 may extend from recesses formed in the vehicle body 300. The levers 360 are controlled by a battery powered hydraulic system 370 that, if needed, can be activated by the operator so that the levers will extend beyond the vehicle body 305 and right the vehicle 300 when the vehicle 300 has flipped over. The system 370 is independent of the drive system of the vehicle 300.

Figure 8:
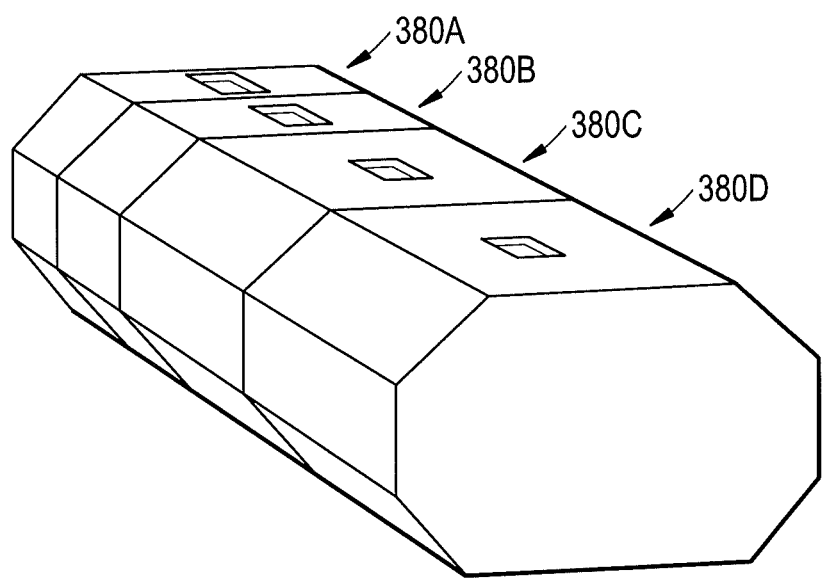
FIG. 8 shows a plurality of modular internal compartments that can be incorporated into the vehicle of FIG. 5.

As shown in FIG. 8, in order to add to the performance and serviceability of the vehicle 300, a plurality of modular internal compartments 380A-380D can be joined to add a wide range of engine and drive systems. FIG. 8 shows, for example, an oil system compartment 380A, a fuel system compartment 380B, a drive system compartment 380C, and a drive or engine compartment 380D. In addition, with the use of the compartments 380A-380D, and the jib crane 340 assembly, such compartments can be added/removed quickly from the primary frame assembly. The advantages of this design allows the engine assembly to be quickly removed and replaced, and thus the vehicle can be returned to service quickly. Another advantage is that the compartmental design allows additional protection to the internal components from weapon damage, even more so if made with high-strength steel. With the engine compartment removed, the covers 365 (see FIG. 6) can be unbolted to allow the service technician to have better access to each section. As an example, if needed, the engine can be replaced by a different drive system, specifically; the diesel engine can be removed and replaced by a battery-powered motor. Such a task can be done very quickly, and with less skill required. For ease of removal and installation, all connections can be color-coded.

FIGS. 9A-11 show a further embodiment consistent with the present disclosure for helping soldiers who have become amputees, paralyzed or injured, wherein modifications can quickly be adapted to a commercial construction vehicle, for example, such as a backhoe/loader vehicle 600. More specifically, with both manual and robotic controls the backhoe/loader vehicle 600 can be used as a construction tool that will help soldiers to regain community re-integration and thus gain quality back into their lives.

Figure 9A:
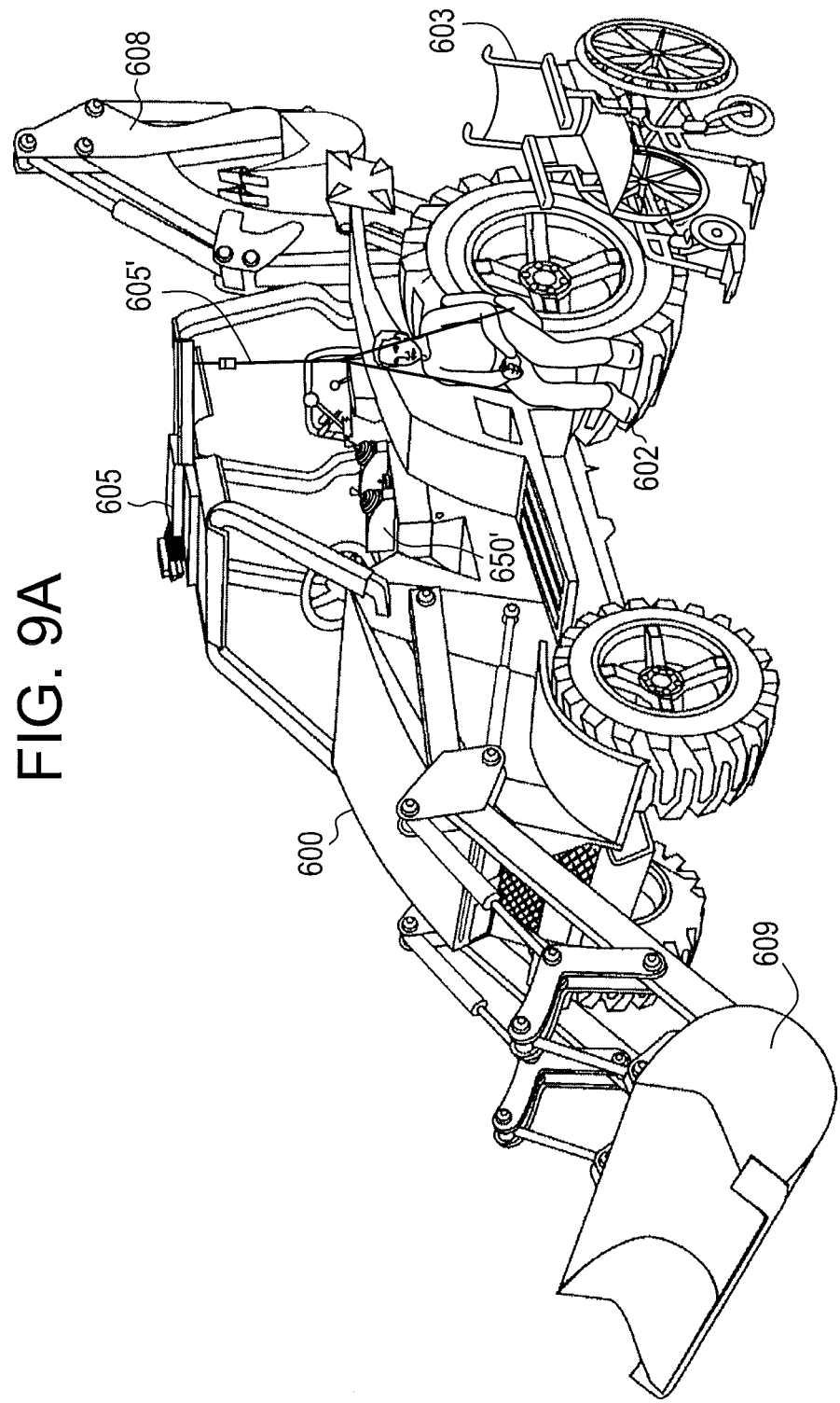
FIG. 9A shows a further embodiment consistent with the present disclosure for helping users who have become amputees, paralyzed or injured according to an illustrative embodiment.

As shown in FIG. 9A, the backhoe/loader vehicle 600 is a fully functional construction vehicle that is modified to support soldiers who have lost their legs or have been paralyzed. The backhoe/loader vehicle 600 allows the user to either operate the vehicle from a distance (via cameras, such as the camera 209 shown in FIG. 2A), or actually be lifted into the operator's seat and travel with the vehicle. Thus, the operator can have either manual or robotic control. In addition, the vehicle can be used and operated with the standard controls as a standard backhoe/loader vehicle.

The backhoe/loader vehicle 600 can be operated in a robotic control mode, as follows:

1. Once in position, the user (e.g., amputee soldier), stops his modified pickup truck or van and exits from the operator's seat.
2. The user then de-activates, via a control system, the binding mechanism that holds the backhoe/loader to the trailer. From the robotic control panel, the user starts the backhoe/loader and backs it off the trailer.
3. With the backhoe/loader vehicle 600 running, the user 602 drives the vehicle to the desired position.
4. With the vehicle in position, the user activates the camera systems and properly sets the backhoe/loader's outriggers into place.
5. At that time, the backhoe 608 of the backhoe/loader vehicle 600 can be controlled by the robotic control panel to dig the trench.
6. As the need arises, the backhoe/loader vehicle 600 can be moved forward to the next position.
7. Steps 5-8 will continue until the task is completed.
8. As needed, the front loader 609 can be controlled to load and/or remove dirt or debris.
9. Once done, the vehicle 600 is transported to the user's trailer, loaded, and then bound into position to be towed.
10. The user then enters into his own vehicle and leaves.

The backhoe/loader vehicle 600 can be operated in a manual control mode, as follows:
1. Once in position, the user (e.g., amputee soldier), stops his modified truck or van and exits from the operator's seat.
2. The user then de-activates, via a control system, the binding mechanism that holds the backhoe/loader vehicle 600 to the trailer. From the robotic control panel, the user starts the backhoe/loader vehicle 600 and backs it off the trailer
3. With the backhoe/loader vehicle 600 off the trailer, the user activates a lifting system 601 operative to pickup and place the user 602 in the operator's seat position 660 of the backhoe/loader vehicle 600.

Figure 10:
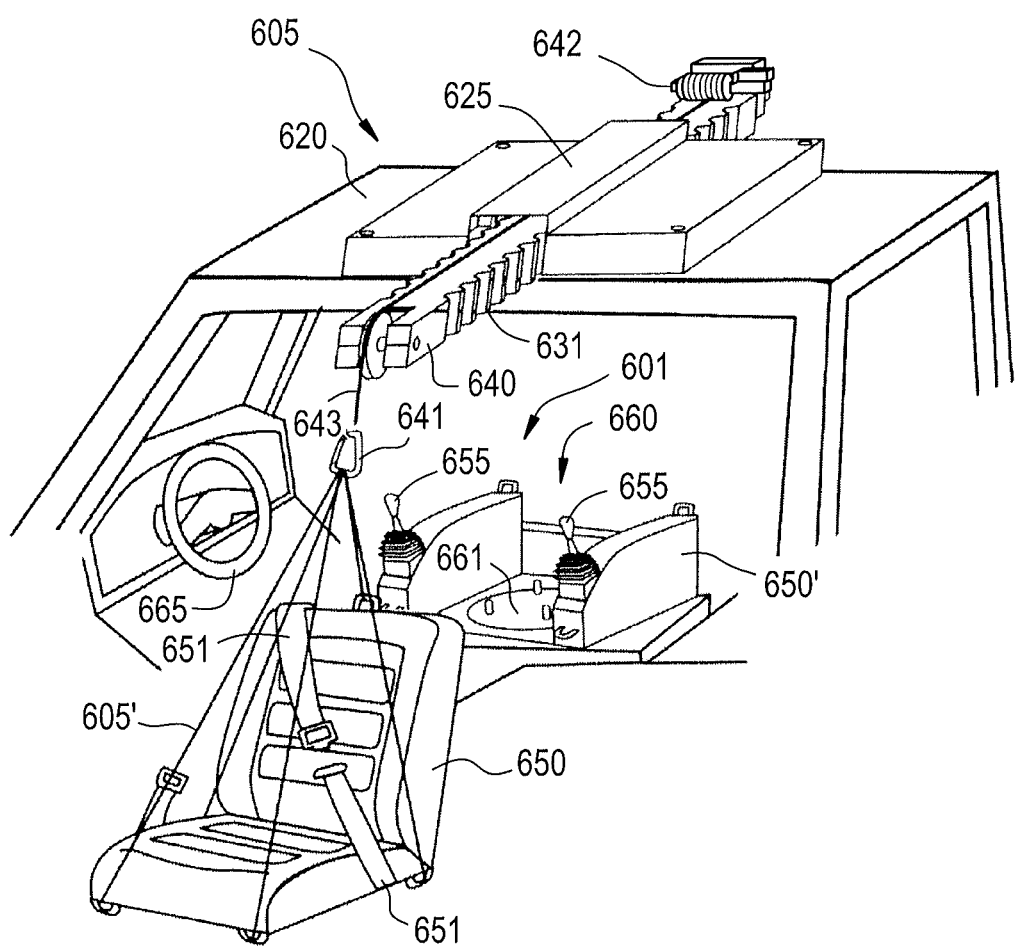
FIGS. 10 and 11 show the lifting mechanism including the rack and pinion mechanism.
Figure 11:
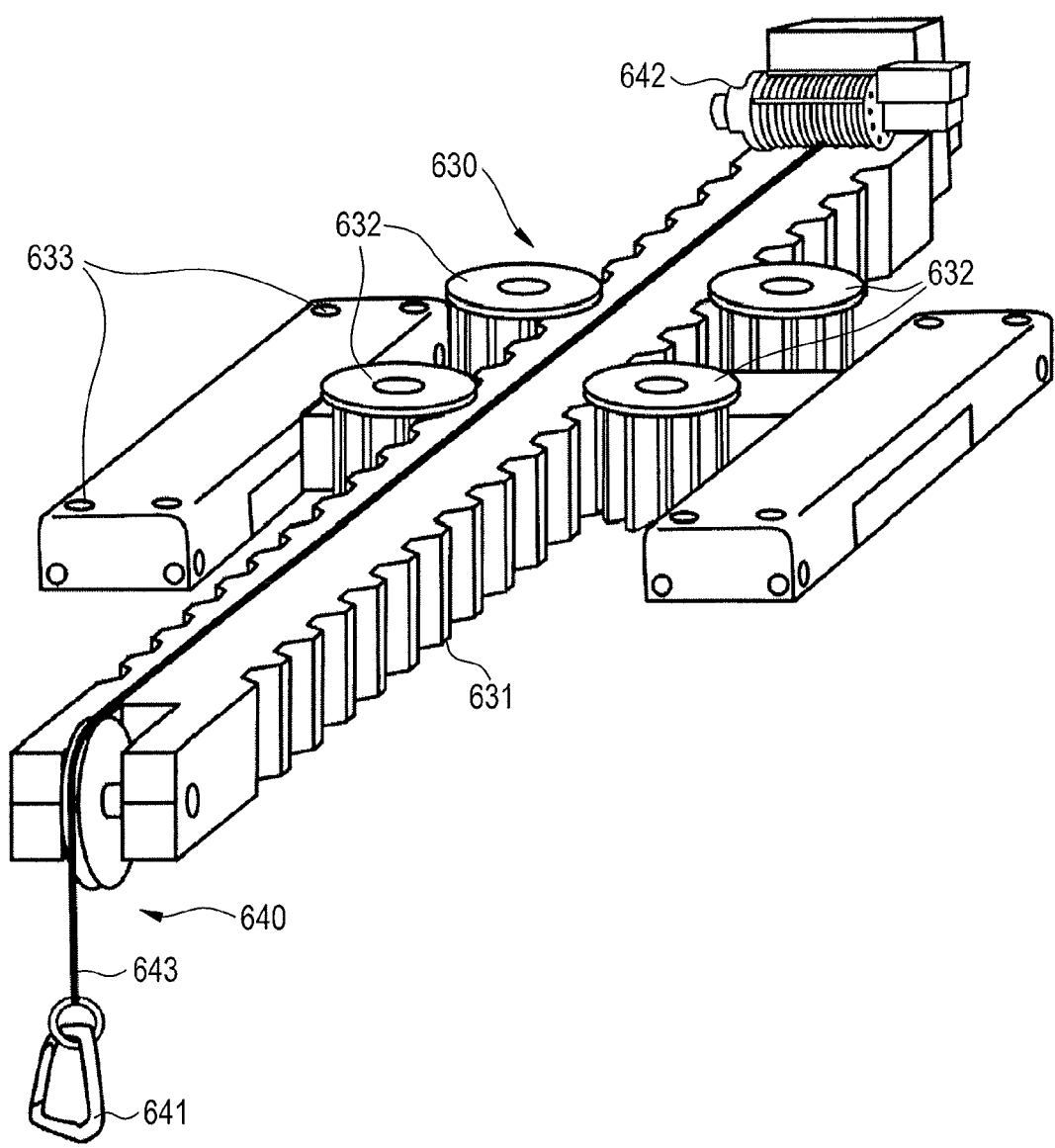

As best shown in FIGS. 10 and 11, the lifting mechanism 605 comprises a rack and pinion mechanism 630 that is designed to be bolted as shown at 633 onto the top of the Roll-Over Protective Structure (ROPS) 620 of the backhoe/loader vehicle 600. The rack 631 is moved by rotation of the pinion gears 632 to position the lifting assembly 605 including a crane assembly 640 over the wheel chair 603. The rack 631 is supported by the ROPS 620 for movement along a channel 625 that is secured to the ROPS 620. At least one of the pinion gears 632 is motor driven by a rotary motor (located beneath the rack and pinion mechanism 630) from DC power provided by the battery of the backhoe/loader vehicle 600. The crane 640 includes a motor driven winding drum 642 for winding up or letting out a lifting cable 643 having a hook or clip 641 mounted on the end thereof. Again, power is supplied by the vehicle battery to drive, for example, a rotary electric motor for winding and unwinding the cable 643 on and from the drum 642.

The steps for positioning the user 602 into the backhoe/loader vehicle 600 are as follows:

The user 602, while in his wheelchair 603, positions himself beside the backhoe loader vehicle 600, as shown in FIG. 9A.

Figure 9B:
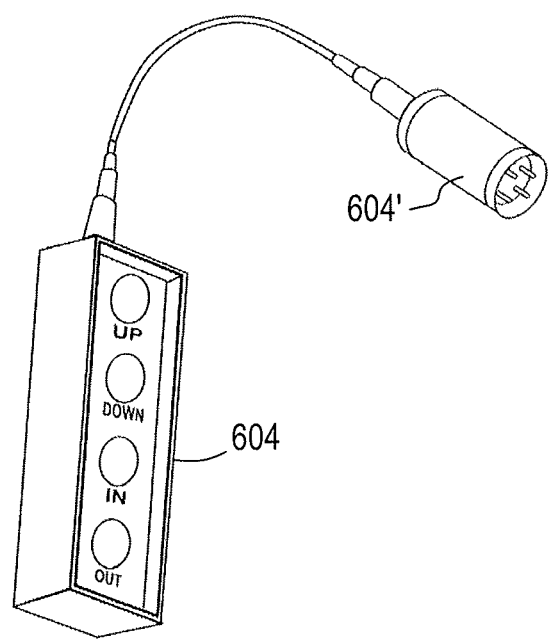
FIG. 9B shows a handheld control system for the lifting mechanism of FIG. 9A.

The user 602 plugs a handheld control system 604 (see FIG. 9B) for the lifting mechanism 605 into the backhoe/loader vehicle 600. The plug receptacle for receiving the plug 604' may be conveniently located in an accessible location on the backhoe/loader vehicle 600 for the user 602 to reach from his wheelchair and from the seat position 660. As shown in FIG. 9B, the handheld control system 604 has four buttons; namely, Up/Down/In/Out.

The user 602 activates the crane assembly 640 of the lifting mechanism 605 to extend from the top of the backhoe/loader vehicle 600, and then the user 602 activates the lifting assembly 605 to lower down the crane hook or clip 641 to within his reach.

The user 602 then attaches the crane hook or clip 641 of the lifting mechanism 605 to his modified wheelchair compatible seat 650, and then disconnects the locks that hold the seat to the wheelchair frame (for example, a known lift-and-turn draw latch or a compression spring draw latch can be used for the seat locking system per se). Note that the wheelchair compatible seat 650 is shown in FIG. 10 attached to the lifting mechanism 605 without the user 602 therein for ease of understanding. The user 602 then attaches the seatbelts 651 to the wheelchair compatible seat 650.

The user 602 then activates the lifting assembly 605 and is lifted up from his wheelchair 603, as shown in FIG. 9A.

To properly allow for the user's wheelchair compatible seat 650, the backhoe/loader seat is made so that its seat and locking system are identical to that of the wheelchair 603. If needed, this seat assembly can quickly be removed and replaced with a conventional seat. This will allow other operators to use the backhoe/loader vehicle 600, if needed.

Once in position over the backhoe/loader's seat position 660, the user will lower himself into the seat position 660 to a seat mounting base 661. Once in position, the user 602 then locks his seat 650 into position (again using a lift-and-turn draw latch or a compression spring draw latch) and removes the hook or clip 641 of the lifting assembly 605. The user 602 then places the harness portion 605' of the lifting assembly into a storage compartment adjacent to the seat. The user 602 can then retract the crane assembly 640 so that the assembly does not extend beyond the backhoe/loader vehicle 600 frame. The user 602 can then place the handheld control system 604 in a stored position.

Figure 9C:
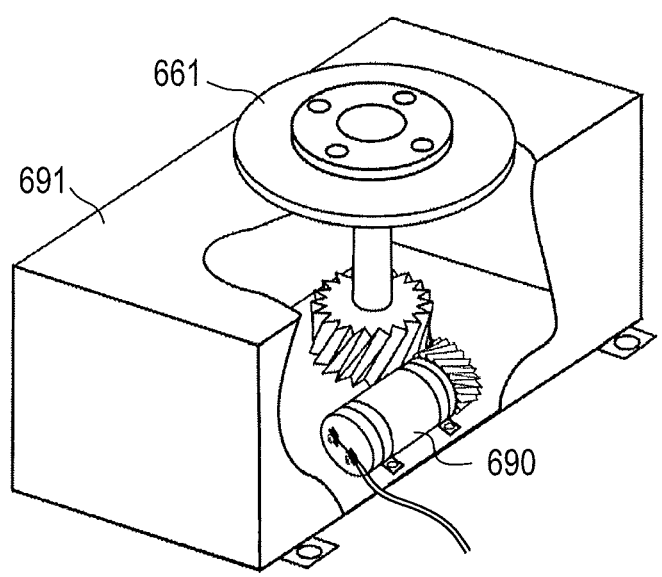
FIG. 9C shows an exemplary embodiment for rotatably mounting the seat mounting base.

In order to allow for operation, the backhoe/loader wheelchair compatible seat assembly base 650' can have two joystick controls 655. Each of the joystick controls 655 can have functions that are the same as that of the robotic control panel (not shown). The steering wheel 665 can quickly be removed if needed to support the user 602. With the user 602 in place and properly bound to his wheelchair compatible seat 650, he can start the backhoe/loader vehicle 600. With user 602 in position and the backhoe/loader in operation, then the user, via the joysticks 655, can move the backhoe/loader vehicle 600 to the needed location. Once in location, the user can operate the backhoe/loader vehicle 600 to perform the needed tasks of either a front loader 609 or a backhoe 608. The wheelchair compatible seat assembly 650/650' can be powered to rotate between the front loader and backhoe operator positions. This control is located on one of the joystick controls 655 on the user's seat. As shown in FIG. 9C, the seat mounting base 661 can be rotated using a battery powered drive motor 690 located beneath the seat mount and housed in a box-shaped cover 691.

With the construction task completed, the user then drives the backhoe/loader 600 to adjacent to the transportation trailer and, once in position, the user places the backhoe/loader vehicle 600 into position for transportation and parallel to his wheelchair. User then turns off the backhoe/loader and then plugs the handheld control system 604 into position. The user installs and lowers the harness 605' of the lifting assembly 605 to his seat and then unlocks the seat locks from the backhoe/loader vehicle 600. The user then raises himself up.

The user then extends the crane assembly 640 so that he is directly in position over his wheelchair 603, and then lowers himself into his wheelchair 603 assembly. The user 602 then locks his seat 650 into the wheelchair 603. The user 602 disconnects the lifting assembly 605 from his wheelchair compatible seat 650, and then raises the crane hook 641 of the lifting assembly 605 to be clear of himself and retracts the crane assembly 640 so that it does not extend beyond the frame of the backhoe/loader vehicle 600. The user 602 then unplugs the handheld crane control system 604.

Once the user is clear, he then starts the backhoe/loader vehicle 600 via the robotic control panel, and trams the backhoe/loader vehicle 600 into position and places the backhoe/loader vehicle 600 onto the trailer assembly. Once the backhoe/loader vehicle 600 is in position on the trailer, the user activates trailer binding mechanisms (not shown) to secure the backhoe/loader vehicle 600. The user then enters into his modified pickup truck or van and leaves.

Figure 12:
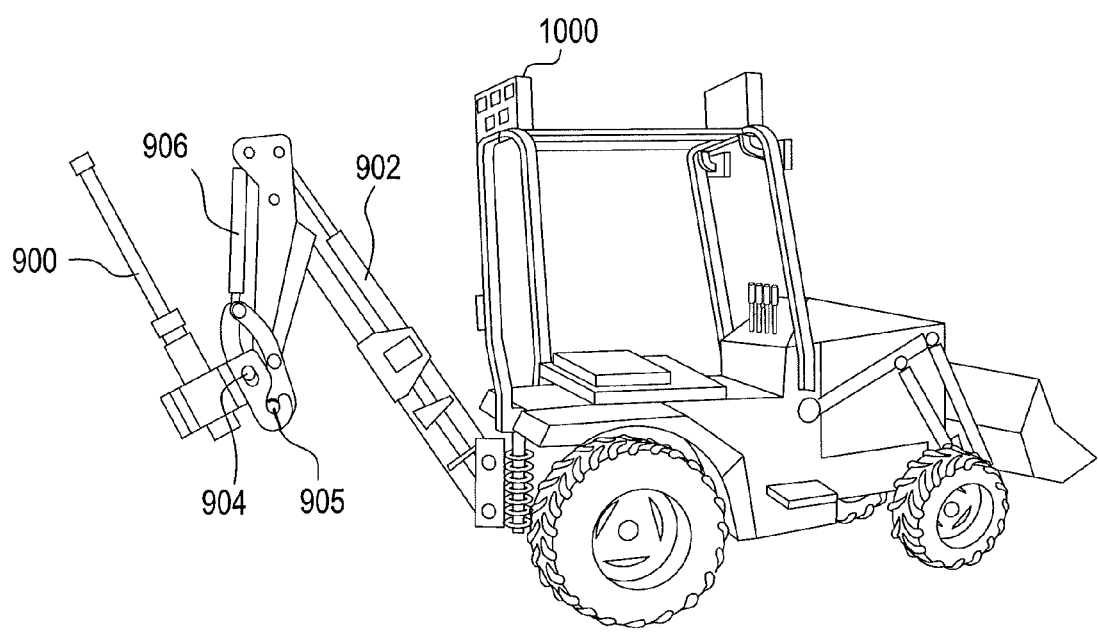
FIG. 12 shows a sensor system for detecting, for example, IEDs or landmines, that can be added to a standard commercial vehicle according to an illustrative embodiment.

FIGS. 12-18 show a sensor system for detecting, for example, IEDs or landmines, that can be added to a standard commercial vehicle, to a motorized vehicle as disclosed in my U.S. Pat. No. 7,565,941, or to the multitask vehicle according to the present disclosure. The vehicle can be operated both manually and via remote (robotic) control. FIG. 12 shows the landmine sensor system 900 mounted on a standard backhoe loader arm 902. The landmine sensor system 900 is attached to the backhoe loader arm 902 by removing the standard backhoe digging bucket. The digging bucket is attached to the backhoe assembly by a single, removable holding pin 904. Removing the single pin 904 allows the bucket to swing clear of a second holding pin 905 (also referred to as the arc swing point) which is formed as fixed part of the backhoe loader arm 902. To mount the detection system 900, the assembly is swung onto the second holding pin 905 at the arc swing point 910, and then the backhoe curl cylinder 906 lifts and holds the assembly 900 in place so that the removable holding pin 904 can be re-installed through the holding pin opening 920. Thus, the procedure can be carried out with no tools in less than a minute by simply removing a single pin 904.

Figure 13:
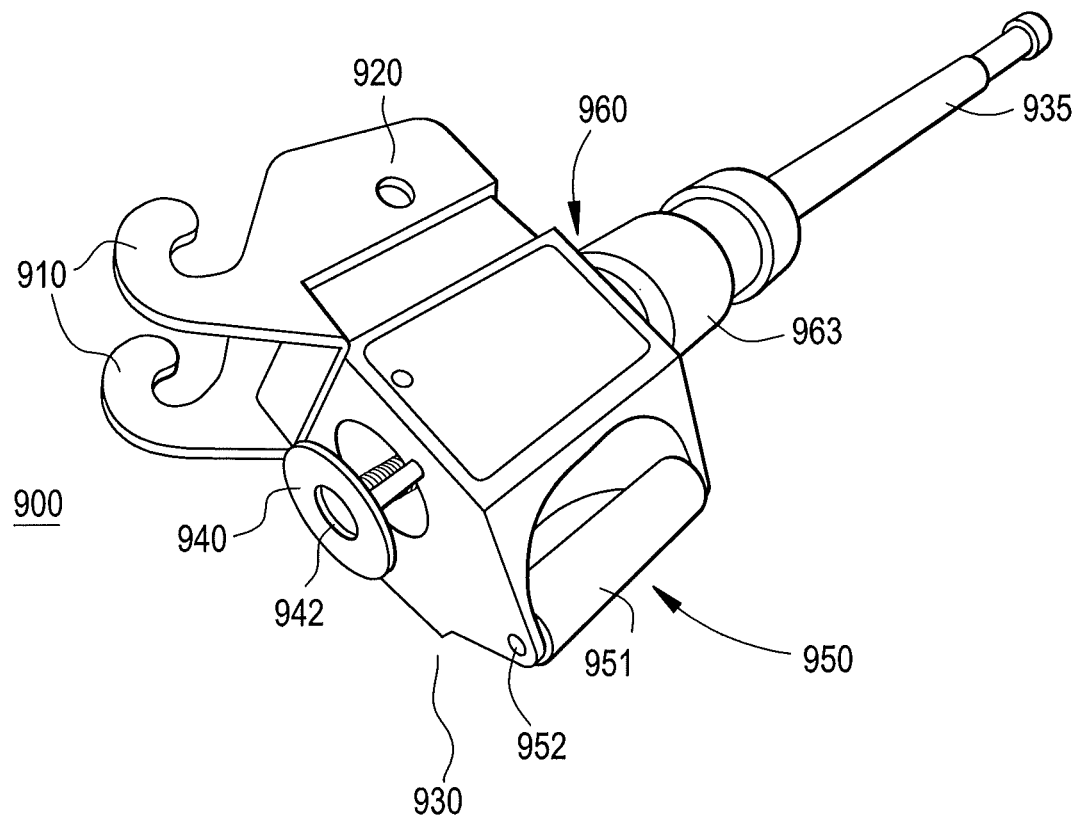
FIG. 13 shows the sensor system removed from the backhoe loader arm of FIG. 12.
Figure 14:
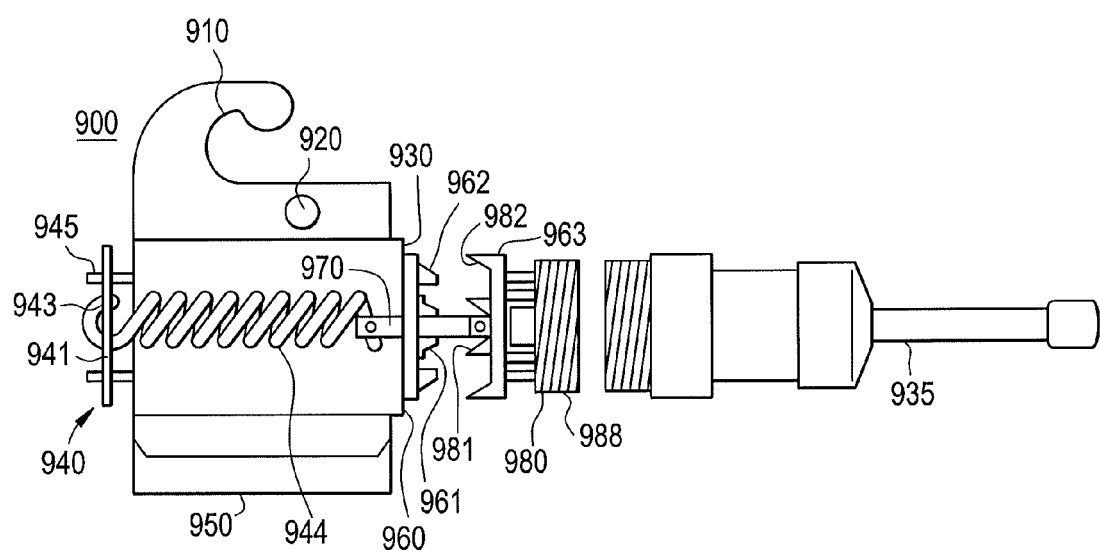
FIG. 14 is an exploded partial cutaway view of the sensor system.
Figure 15:
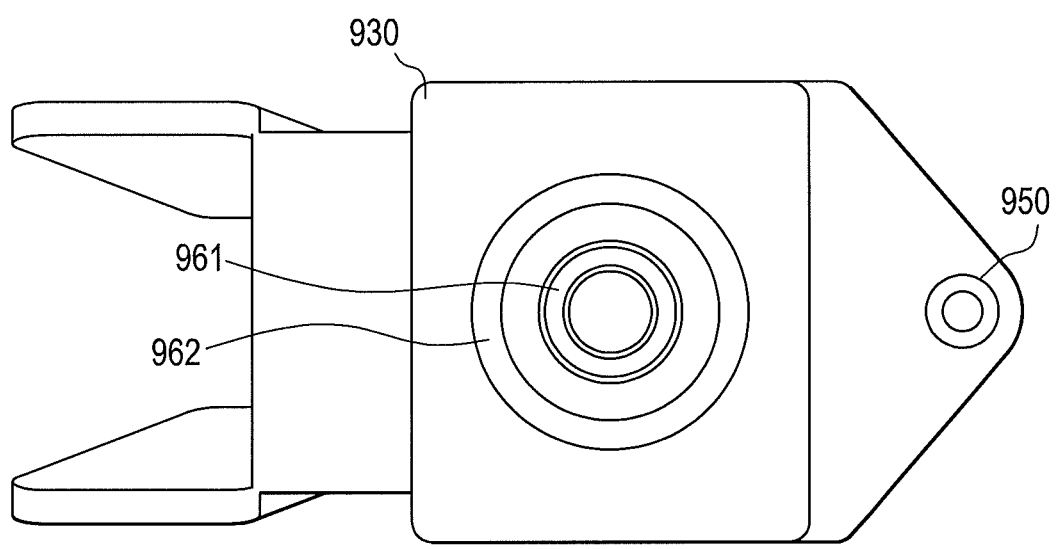
FIG. 15 is an front end view of the mounting portion of the sensor system.

FIGS. 13-15 show the sensor system 900 removed from the backhoe loader arm 902, including a mounting portion 930 formed of, for example, metal. As shown in FIG. 13, the arc swing points 910 and one of the holding pin openings 920 are shown. The sensor or detection wand arm assembly 935 extends from the mounting portion 930 and is joined to the mounting portion 930 by an adaptor 980 and a spring assembly 940 which, as will be discussed in more detail below, allows for lateral movement of the sensor or detection wand arm assembly 935. A roller assembly 950 is disposed at the bottom of the mounting portion 930 and comprises a tube 951 held in place by a single pin 952. The roller assembly 950 facilitates the mounting portion 930 in passing over obstacles that may be embedded in the ground as the backhoe arm 902 swings back and forth as described in more detail below. Also, a tooth assembly (not shown) can be advantageously added to the lower portion of the mounting portion 930 to allow debris to be picked up and moved.

Once the sensor system or assembly 900 is mounted to the backhoe arm 902, the spring tension is set to protect the electronic detection wand arm assembly 935 as the backhoe arm 902 swings from right to left (e.g., in case the electronic detection wand arm assembly 935 impacts a protruding obstacle in the area being cleared). As noted above, the spring assembly 940 is mounted at the rear of the mounting portion 930. With reference to FIGS. 13 and 14, the spring assembly 940 comprises an outer plate 941 with an inner circle 942 that holds one end 943 of the spring 944. The other end of the spring 944 is attached to a rod 970 which in turn is connected to one end of the adaptor 980. The adaptor 980 is engaged with a front portion 931 of the mounting portion 930 by using matching pairs of an inner tapers and outer tapers. The outer taper 962 of the mounting portion 930 is machined to match an outer tapered portion 982 of a steel taper mount cover 963, and the inner taper 961 of the mounting portion 930 is machined to correspond to an inner tapered portion 981 of the steel taper mount cover 963 thereby to limit the travel of the wand assembly 935 (see FIGS. 14 and 15). As noted above, the central part of the steel taper mount cover 963 of the adaptor 980 is fastened (e.g., using a bolt) to the spring biased rod 970. The outer end of the steel taper mount cover 963 of the adaptor 980 is bolted by a plurality of bolts 985 to an inner adaptor mount portion 988 which in turn is threaded using male or outer threads to female or inner threads of the wand arm assembly 935.

To adjust the tension, the outer plate 941 is held in place by a plurality of adjustable fasteners such as bolts 945 (for example, three) that allow the operator to move the outer plate 941 closer to or apart from the rear 932 of the mounting portion 930 to set spring tension. Specifically, extending the outer plate 941 away from the rear 932 of the mounting portion 930 increases spring tension, and reducing the distance between the outer plate 941 and the mounting portion 930 reduces spring tension, thereby to adjust the amount of lateral movement of the wand arm assembly 935.

The spring tension of spring 944 is initially set to allow the wand arm assembly 935 to be installed. Once the wand arm assembly 935 is installed, tension will be set to allow the best level of protection to the electronic sensor wand system. Examples of tight spring tension may be in urban environments where the operator can see, from a safe distance, any vertical uprights that may damage the wand system. Less spring tension would be applicable to areas where plant or brush growth may limit the operator's field of view. An option is to add a series of electronic proximity switches between the wand system and mounting portion 930, for example, within the mounting portion 930 as at location 960. The proximity switches are set to stop the swing of the backhoe assembly, or to cause the backhoe to reverse motion, to prevent damage to the detector wand assembly 935. Suitable proximity switches per se that may be used are available in, for example, the automobile industry. An audible alarm could also be triggered by the proximity switches to alert the operator of the vehicle. Such switch signals are integrated into the vehicle command modules and, based upon set parameters, reverse the direction of the backhoe arm assembly, via the hydraulic control valve assembly.

In operation, the sensor wand arm assembly 935 provides an output to indicate signal strength and polarity. When the sensor wand arm 935 is directly over a target with a positive signal polarity, the digital signal peaks and then an output signal returns to zero, as the sensor wand arm 935 passes over the buried explosive device until it reaches the edge of the buried device, at which time the wand will then signal a negative polarity. By the wand showing a peak in signal strength, this marks the beginning of the buried object, and as the signal polarity changes this will then mark length of any buried object. While an example of a sensor wand operation is described, the present disclosure is not limited to this particular type of sensor or detector. The sensor wand arm assembly 935 may be protected by an ultra high molecular weight polyethylene (UHMW) plastic cover.

Figure 16:
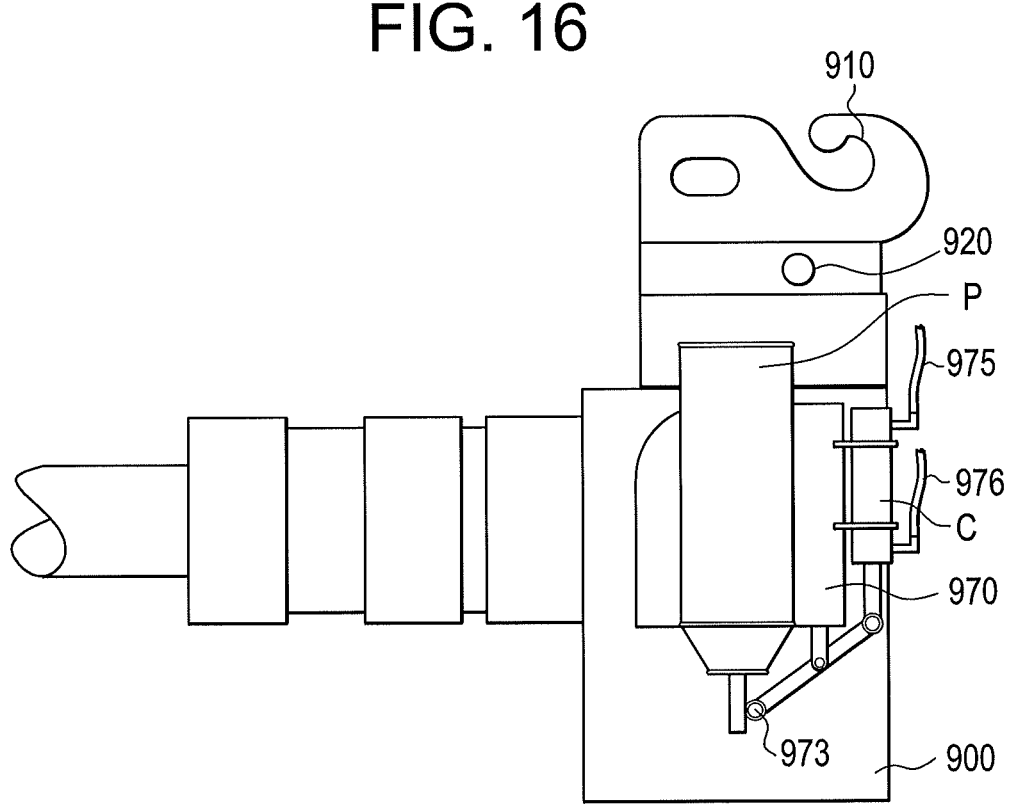
FIGS. 16 and 17 show a paint marking holder to be used with the sensor system.
Figure 17:
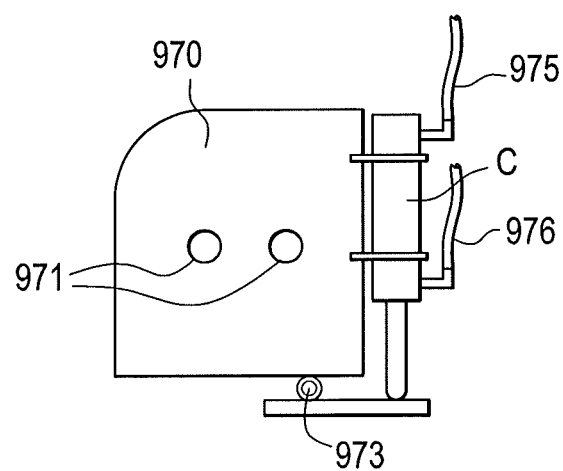

As shown in FIGS. 16 and 17, a paint marking holder 970 can be mounted, for example, to the side of the mounting portion 930, and holds paint can P used for marking both cleared areas and possible IEDs.

As shown in FIG. 17, the holder 970 includes a mount formed by a tandem set of holes 971 on each side (only one side shown) to allow right or left mounting. The mount can be held in place by set of magnetic bolts that are first bolted to the holder 970, and then the holder 970 is placed into position on the mounting portion 930. The holder 970 can also be bolted to end of the backhoe arm using threaded holes formed therein such that the holder 970 is thus bolted into place onto the vehicle.

Once the holder 970 is in position, a paint can mount is loosened to allow the paint marker can P to be installed (see FIG. 16 which has the side panel removed for ease of understanding). The paint can P is positioned such that a nozzle of the paint can C is bearing against a cylinder pivot point 973. A marking cylinder C is used to move levers 977 and 978 to activate the cylinder pivot point 973 to in turn open the paint can nozzle by, for example, pushing the nozzle sideways to release the paint from a pressurized paint can P. FIG. 17 shows an alternative lever arrangement for opening the paint can nozzle. Although one color of paint is shown (i.e., one paint can P), alternatively, two colors of paint can be used by mounting holders 970 on both sides of the mounting portion 930, with one color being used to mark the area clear, and the other color being used to mark a buried explosive device and/or a detected signal that indicates a possible explosive device such as an IED.

With the holder 970 in position and paint can P installed, two hydraulic hoses 975 and 976 that are connected to the marking cylinder C are connected to the backhoe control valve system. The backhoe control valve system is controlled by an electro-hydraulic set of commands from the main system module.

Alternatively, a standard commercial highway line painting device can be mounted on the vehicle and used for marking the area to be cleared of IEDs or landmines.

As the backhoe assembly swings from right to left, the operator and/or the system will mark the extent of the backhoe arm's 902 swing. If done by the operator, the operator activates this function from the remote control panel he is holding. If done by the vehicle, the main command module will activate the marking cylinder C from parameters input by the operator. The operator can set the time for the signal to activate the cylinder, since different terrains may require variation of marking time; for example, urban areas may only require a short burst of paint while overgrown areas may need longer times.

Figure 18:
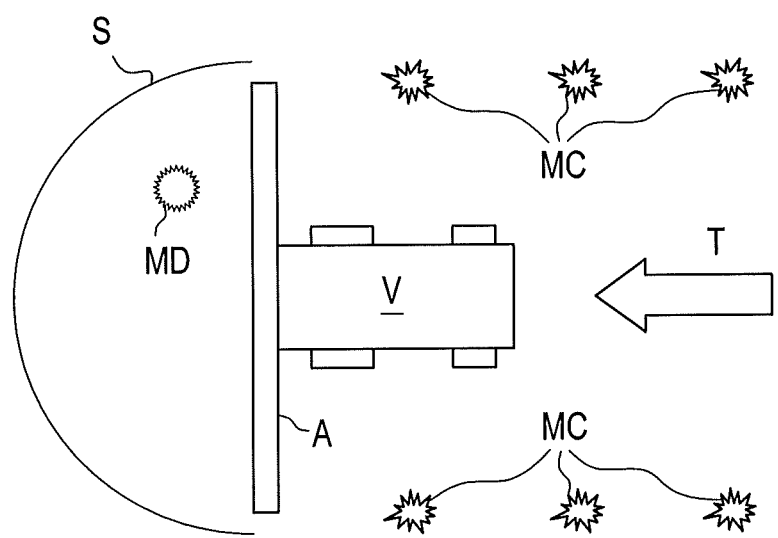
FIG. 18 is an overhead view of the marking system and showing the arc when the backhoe arm swings the sensor wand assembly from side to side.

FIG. 18 is an overhead view of the marking system and showing the arc when the backhoe arm A swings the sensor wand assembly from side to side. For example, the vehicle V can have a swing S of 22 feet. As the vehicle V moves in direction T a possible IED is marked with, for example, red paint as shown at mark MD. On the other hand, the area behind the vehicle V in the direction of travel T is marked as clear using a different color paint such as green paint as shown at marks MC. Moreover, while paint is shown, other physical indicators could also be used. With the marks thus made, an anti-mine technician can use the proper method to remove the buried device. As an option, a remote controlled assembly can be activated that will drop a small explosive charge onto the spot where a buried device has been detected. A delay will be given to allow the vehicle to move away for protection. At a set point, the dropped charge will detonate and thereby cause the buried device to explode also. In this way, both the operator and the vehicle V are protected.

Moreover, as shown in FIG. 12, a plurality of indicator lights 1000 can be positioned on the frame of the vehicle to indicate the strength of the signal of the sensor system 900. For example, the plurality of indicator lights comprises five indicator lights, the number of which indicates the signal strength of between 1-5, with 5 illuminated lights being the strongest signal. The lights allow the operator to determine the potential of buried explosive devices. The lights are connected either by electrical hard wire or wirelessly to the detecting sensor or sensors of the sensor wand arm 935. The lights can be positioned at various locations on the vehicle to maximize ease of visual observation. A range exceeding 1500 feet can be obtained for visual observation of the indicator lights 1000 by, for example, military personnel. In this regard, existing technology allows for a remote link to be installed between the transmitter and receiver. This link serves as a two-way communication channel so that the operator can view signal strength at a safe distance. See, for example, the TraceMaster II Pipe & Cable Locator from Schonstedt Instrument Company. Such a system has an operating range of up to 1500 feet.

An electric sensing system can be included to maintain a constant height of the backhoe arm 902 as it swings back and forth, thus ensuring a consistent signal to ground height. The electric sensing system can include a series of sensors placed directly under the adaptor assembly which is located between the sensor or detection wand arm assembly 935 and the mounting portion 930. The electric sensing system operates on a similar principle to the electronic backup sensing system of an automobile. The electric sensing system can be integrated into the electro-hydraulic control system.

By the use of the backhoe arm 902 assembly, the vehicle can be used to scan over obstacles, up and down slopes, and over open areas. Moreover, the vehicle can be quickly converted back to a construction vehicle by simply removing the pin 904 and replacing the sensor assembly or system 900 with a backhoe bucket.

The present invention has substantial opportunity for variation without departing from the spirit or scope of the present invention. For example, while the embodiments discussed herein are directed to military and rescue settings, the present invention is not limited thereto. For example, the vehicles could be used in construction, police or by firemen. Moreover, clearly the various features of this disclosure can be used among the various embodiments. For example, the landmine sensor system 900 can be used on the multitask vehicles of FIGS. 1-11 by simply replacing the backhoe digging bucket with the sensor system 900 as explained herein.

Those skilled in the art will recognize improvements and modifications to the preferred embodiments of the present invention. All such improvements and modifications are considered within the scope of the concepts disclosed herein and the claims that follow.

What is claimed is:

1. A lifting system in combination with a construction vehicle, for lifting a person into the construction vehicle for operation thereof, comprising:
    a wheelchair compatible seat which is operative to detach from a wheelchair; and
    a lifting mechanism comprising a rack and pinion mechanism that is mounted to a top portion of the construction vehicle, a rack portion of the rack and pinion mechanism being movable outwardly and inwardly with respect to a side of the construction vehicle, a crane assembly disposed on the rack portion of the rack and pinion mechanism and having a lifting cable with a clip mounted on an end of the lifting cable, and a lifting harness connected to the wheelchair compatible seat and operative to be connected to the clip,
    wherein when the clip is connected to the harness of the wheelchair compatible seat, the crane assembly of the lifting mechanism is activated and the wheelchair compatible seat is lifted up from the wheelchair, moved inwardly by the rack portion to a seat position of the construction vehicle, and then lowered into the seat position.

2. The lifting system in combination with a construction vehicle of claim 1, wherein the rack and pinion mechanism is disposed in a housing mounted onto a top of a Roll-Over Protective Structure (ROPS) of the construction vehicle.

3. The lifting system in combination with a construction vehicle of claim 1, wherein the crane comprises a motor driven winding drum for wing up and letting out the lifting cable.

* * * * *